United States Patent [19]

Chang et al.

[11] Patent Number: 4,914,170

[45] Date of Patent: Apr. 3, 1990

[54] SUPERABSORBENT POLYMERIC COMPOSITIONS AND PROCESS FOR PRODUCING THE SAME

[75] Inventors: Ching-Jen Chang, Chalfont; Walter DeWitt, Southampton, both of Pa.

[73] Assignee: Rohm and Haas Company, Philadelphia, Pa.

[21] Appl. No.: 121,567

[22] Filed: Nov. 17, 1987

[51] Int. Cl.$^4$ .................. C08F 30/04; C08F 20/04; C08F 18/00

[52] U.S. Cl. ................. 526/240; 526/317.1; 526/318.3; 526/320

[58] Field of Search ............ 526/240, 317.1, 318.3, 526/320

[56] References Cited

U.S. PATENT DOCUMENTS

| | | | |
|---|---|---|---|
| 3,935,099 | 1/1976 | Weaver et al. | 210/43 |
| 4,167,464 | 9/1979 | George | 204/159.23 |
| 4,286,082 | 8/1981 | Tsubakimoto et al. | 526/210 |
| 4,473,689 | 9/1984 | Login et al. | 526/91 |
| 4,483,950 | 11/1984 | Fanta et al. | 524/48 |
| 4,551,191 | 12/1985 | Kock et al. | 156/276 |
| 4,558,100 | 12/1985 | Kightlinger et al. | 525/329.1 |
| 4,587,319 | 5/1986 | Tournier | 527/313 |
| 4,610,678 | 9/1986 | Weisman et al. | 604/368 |
| 4,613,543 | 9/1986 | Dabi | 428/304.4 |
| 4,650,716 | 3/1987 | Gelman | 428/402 |
| 4,654,039 | 3/1987 | Brandt et al. | 526/207 |
| 4,670,011 | 6/1987 | Mesek | 604/378 |
| 4,673,402 | 6/1987 | Weisman et al. | 604/368 |
| 4,676,784 | 6/1987 | Erdman et al. | 604/368 |

Primary Examiner—Joseph L. Schofer
Assistant Examiner—N. Sarofim
Attorney, Agent, or Firm—Carl W. Battle

[57] ABSTRACT

Superabsorbent polymeric compositions are prepared from monomer including acrylic acid and an effective amount of a second hydrophilic monomer, which can be a soluble salt of beta-acryloxypropionic acid. Preferably, the pH of the aqueous monomer solution is adjusted to substantially exclude free acid, and the aqueous monomer solution is coated onto a heated surface to both polymerize the monomer and dry the resulting hydrogel. Free acid thermal degradation products are avoided and the superabsorbent product has greater absorption capacity than acrylate homopolymer.

13 Claims, No Drawings

SUPERABSORBENT POLYMERIC COMPOSITIONS AND PROCESS FOR PRODUCING THE SAME

BACKGROUND OF THE INVENTION

1. Field of the Invention

The present invention relates generally to polymeric compositions for use as absorbent materials for aqueous fluids and to a process for the preparation of these compositions; and more specifically to improved superabsorbent polymeric compositions prepared from monomer including water soluble acrylate salt.

2. Brief Summary of the Prior Art

"Superabsorbents" are water insoluble materials which are capable of absorbing and retaining large amounts of water or other aqueous fluids in comparison to their own weight. The term "superabsorbent" is commonly used in the industry to refer to materials capable of absorbing at least fifteen times their own weight. Superabsorbents are used in a variety of disposable diaper and catamenial products. Disposable goods manufactured using superabsorbents can be more comfortable, less bulky, and longer lasting than similar products made with traditional absorbents such as cellulose fibers. Disposable diapers and catamenial products containing superabsorbents are disclosed, for example, in U.S. Pat. Nos. 4,676,784, 4,673,402, 4,670,011 and 4,610,678. Superabsorbents can be supplied in a variety of physical forms including free-flowing powders. Superabsorbents are typically hydrogel-forming polymer compositions: hydrophilic polymeric compositions which are crosslinked to insolublize them. Synthetic polymeric compositions prepared from monomer which includes a carboxylate functional group, such as sodium acrylate, are commercially important superabsorbents. Synthetic polymeric superabsorbents are well known in the art, and are disclosed for example, in U.S. Pat. No. 4,286,082 (acrylic acid, alkali metal acrylate, and a crosslinkable comonomer polymerized in presence of surface active agent); U.S. Pat. No. 4,654,039 (low temperature, low concentration polymerization of acid monomers to form high strength hydrogel); U.S. Pat. No. 4,167,464 (photopolymerized copolymers of acrylic acid) ($C_{10}$–$C_{30}$)alkyl(meth)acrylates, and ($C_1$–$C_9$)alkylacrylates); U.S. Pat. No. 4,354,487 (graft-polymerized polyacrylate-cellulose fiber composites); U.S. Pat. No. 4,558,100 (homopolymer of saponified, crosslinked (meth)acrylonitrile); U.S. Pat. No. 4,587,319 (copolymer of acrylic acid and allyl oligosaccharide); and U.S. Pat. No. 4,613,543 (polyacrylate/polyurethane interpenetrating polymer network). Superabsorbents can also be prepared from natural polymeric materials, such as disclosed in U.S. Pat. No. 4,483,950 (dextrin-extended starch-polyacrylonitrile graft copolymer); U.S. Pat. No. 4,650,716 (non-fibrous carboxymethyl cellulose); and U.S. Pat. No. 3,935,099 (starch-polyacrylonitrile). A summary of U.S. patents relating to superabsorbent polymers is given in U.S. Pat. No. 4,551,191 (Column 6). Japanese Unexamined Patent Application No. 56-161412 discloses a water-absorbent resin polymerized from monomer including (meth)acrylic acid and a copolymerizable sulfonic acid.

Ideally, superabsorbents are completely insoluble materials which are highly swellable by urine and other aqueous body fluids. In preparing synthetic polymeric superabsorbents a compromise must be drawn between insolubility and swellability: as the extent to which the polymer is cross-linked increases, the proportion of the polymeric composition which is soluble (soluble fraction) decreases, but so does the swellability and concomitant absorbent capacity of the polymeric composition. Consequently, synthetic polymeric superabsorbents are typically only lightly crosslinked to render them insoluble and have relatively high soluble fractions.

A number of approaches have been suggested for reducing the soluble fraction while only lightly crosslinking the polymer to retain high absorbence capacity. For example, U.S. Pat. No. 4,473,689 discloses minimization of initiator concentration by gradual addition of initiator to the polymerization medium. U.S. Pat. No. 4,654,039 favors polymerizing acidic monomers in their free acid, non-neutralized forms at relatively low polymerization temperatures and at relatively low monomer concentrations.

The polymers can be crosslinked by a variety of means. For example, crosslinking can occur during polymerization through incorporation of copolymerizable vinyl multifunctional comonomer, or subsequent to polymerization by reaction between carboxyl groups pendent from individual polymer molecules and a suitable multifunctional crosslinking agent. According to U.S. Pat. No. 4,286,082 superabsorbents can be prepared by polymerizing acrylic acid which has been at least 50% neutralized to a soluble acrylate salt form.

A polymeric suberabsorbent's capacity to swell is a function of both the average molecular weight of the polymer (assuming an uncrosslinked composition) and the crosslink density. High average molecular weight is correlated with the ability to retain absorbed aqueous fluids against applied pressure. Superabsorbents are generally characterized by the amount of fluid absorbed in a specified time ("capacity") and by the capacity retained once they are swollen and placed under an applied pressure ("retention"). A high average molecular weight is achieved through optimization of polymerization conditions. While ideally each polymer chain should be connected by the minimum number of crosslinks which insures insolubility, in practice a distribution in the number of crosslinks per chain is realized, and maximum swellability occurs while there is yet a significant proportion of uncrosslinked chains. When this soluble fraction is too high, a substantial portion of the polymer composition will dissolve to form a polymer solution and not participate in the desired absorption. The polymer solution will have a high viscosity relative to water or body fluids, and its presence may retard wicking by absorbent structures containing the superabsorbent. The dissolved polymer may even diffuse to the skin where it may cause irritation. Conversely, when a soluble fraction is too low, many chains will have been excessively crosslinked and the swellibility and corresponding absorption capacity will be restricted.

When superabsorbents are polyelectrolytes, such as carboxylate-functional superabsorbents, their absorption capacities depend on the ionic strength of the absorbed aqueous fluids. The absorption of body fluids such as urine and blood, which contain on the order of 1% by weight of various dissolved salts, is substantially less than the absorption of electrolyte-free water.

Polyelectrolyte-type superabsorbents are the most efficient of commerically available materials. They are typically prepared by at least partially neutralizing an aqueous solution of acrylic acid with an alkali metal base, such as sodium hydroxide, and subsequently polymerizing the acrylate monomer. However, the extent to which the acrylic acid is neutralized prior to polymerization represents an undesirable compromise.

In the first place, process considerations suggest that complete neutralization of the acid monomer is undesirable in some processes because phase separation is likely to occur during the polymerization under these conditions. Phase separation may result, depending on the specific process used, in inconsistent production runs, failure to meet specifications, and a host of associated problems. Thus a prudent process would seem to include only partial neutralization of the acid monomer.

On the other hand, the polymerization product is typically dried to a solid and granulated. Residual acrylic acid in the polymer tends to volatilize when the hydrogel is heated. Further, polymerized acrylic acid tends to depolymerize at the elevated temperatures used in drying the product. Because acrylic acid has some toxicity it is desirable to employ additional expensive equipment in the process to control, collect and dispose of the volatilized monomer.

Further, neutralizing the carboxylic acid residues in the polymeric compositions is not always practical, because the product is a hydrogel. Post polymerization neutralization requires additional capital equipment and extends processing time, raising the cost of the superabsorbent product. These considerations counsel that the acid monomer be substantially completely neutralized prior to polymerization.

Given the substantial commercial importance of polyacrylate-type superabsorbents, there is an unmet need for process for producing polyacrylate-type superabsorbents which avoids the pitfalls and compromises of prior art processes, and permits the economical manufacture of high quality superabsorbents, with minimal phase separation, and without requiring additional equipment for collecting and retaining noxious gaseous byproducts of the drying process, or for post-polymerization neutralization.

SUMMARY OF THE INVENTION

The present invention provides a novel superabsorbent polymeric composition and a process for the preparation of this composition. The superabsorbent polymeric composition comprises a substantially water insoluble, hydrogel-forming copolymer polymerized from monomer including at least one first hydrophilic monomer selected from acrylic acid and water soluble salts of acrylic acid, and an amount of at least one second hydrophilic monomer effective to at least reduce, and preferably to prevent, the phase separation of the reaction mixture which would otherwise be observed shortly after the polymerization has begun. Preferably, the at least one second hydrophilic monomer is selected from beta-acryloxypropionic acid ("AOPA"), the water soluble salts of beta-acryloxypropionic acid, 2-hydroxyethyl methacrylate, the $(C_1-C_4)$alkoxy$(C_1-C_4)$alkyl (meth)acrylates, the $(C_1-C_4)$alkoxy-$(C_1-C_4)$alkoxy$(C_1-C_4)$alkyl (meth)acrylates, the mono(meth)acrylate esters of $HO(CH_2CH_2O)_nH$ where n is a positive integer from 2 to about 10, and (meth)acrylate esters of $CH_3O(CH_2CH_2O)_xH$ where x is a positive integer from 2 to about 10. The second hydrophilic monomer is more preferably selected from beta-acryloxypropionic acid, the water soluble salts of beta-acryloxypropionic acid, 2-methoxyethyl acrylate, 2-hydroxyethyl methacrylate, 2-(2-methoxyethoxy)ethyl acrylate and the mono methacrylate ester of a polyethylene glycol having an average molecular weight of about 90. Sodium beta-acryloxypropionate is especially preferred. When a soluble salt of beta-acryloxypropionic acid is used as the second hydrophilic monomer, it is preferred that the second hydrophilic monomer comprise at least about 2%, and more preferably at least 5% by weight of total monomer.

In general the first and second hydrophilic monomers can be dissolved in water to form an aqueous monomer solution. Preferably, the nonionized free acid forms of the monomers, acrylic acid and beta-acryloxypropionic acid, are substantially excluded from the aqueous monomer solution by adjusting the pH. The substantial insolubility of the polymeric material can be achieved by including a copolymerizable crosslinking monomer, such as a monomer including at least two copolymerizable ethylenically unsaturated groups. For example, a polyethylene glycol dimethacrylate can be used.

The process for the preparation of the superabsorbent polymeric compositions of this invention comprises (a) preparing a monomer mixture including at least one hydrophilic monomer selected from acrylic acid and a water soluble salts of acrylic acid, and an amount of at least one second hydrophilic monomer effective to at least reduce, and preferably to prevent, the phase separation of the reaction mixture which would otherwise be observed shortly after the polymerization has began; and (b) polymerizing the monomer mixture. Preferably, the at least one second hydrophilic monomer is selected from beta-acryloxypropionic acid ("AOPA"), the water soluble salts of beta-acryloxypropionic acid, 2-hydroxyethyl methacrylate, the $(C_1-C_4)$alkoxy$(C_1-C_4)$alkyl (meth)acrylates, the $(C_1-C_4)$alkoxy-$(C_1-C_4)$alkoxy$(C_1-C_4)$alkyl (meth)acrylates, the mono(meth)acrylate esters of $HO(CH_2CH_2O)_nH$ where n is a positive integer from 2 to about 10, and the (meth)acrylate esters of $CH_3O(CH_2CH_2O)_xH$ where x is a positive integer from 2 to about 10.

Preferably, as noted above, the pH of the monomer mixture is adjusted to substantially exclude the non-ionized free acid forms of acidic monomers present. The hydrophilic monomers can be dissolved or dispersed in water to form an aqueous monomer solution or dispersion. This aqueous solution or dispersion can be coated onto a heated surface, such as the belt of the belt dryer, or the interior surface of a rotatory drum dryer, the heated surface serving to elevate the temperature of the aqueous monomer solution thereby polymerizing the monomer and drying the polymerized material. Preferably, the superabsorbent polymeric composition is dried to a water content of less than about 20% by weight and is pulverized to form a granular powder. This powder is preferably further dried, if necessary, to give a granular superabsorbent polymeric composition having a water content in the range from about 2 to 7% by weight.

When the process of the present invention is employed, polyacrylate-type superabsorbent can be manufactured with substantially neutralized acid monomer and significant amounts of undesired gaseous byproducts, such as acrylic acid monomer, are not released during drying. In addition, post-polymerization neutralization is not required. Post-polymerization neutralization of hydrogels is difficult to carry out; the polyelectrolyte nature of the hydrogel makes uniform neutralization of the material an uncertain and a time consuming process. Thus the present process fulfills a previously unmet need in the art of manufacturing polyacrylate-type superabsorbent compositions.

In addition, it has been unexpectedly found that the superabsorbent polymeric composition of the present invention exhibit superior capacity for absorption of aqueous fluids in comparison with prior art compositions. This unexpected superiority permits the design and manufacture of disposal diapers, catamenial products and, the like, which are more comfortable, longer lasting, and more effective than prior art products.

DETAILED DESCRIPTION

The polymeric superabsorbent compositions of the present invention are prepared by polymerization of monomer which includes both a first hydrophilic monomer and at least one second hydrophilic monomer. The first hydrophilic monomer is selected from acrylic acid and the water soluble salts of acrylic acid, such as the alkali metal salts of acrylic acid, for example, sodium acrylate and potassium acrylate. Preferably, at least about 60% by weight of the first acid monomer is in the water soluble salt form. However, it is especially preferred that substantially all the first hydrophilic monomer be in the form of a water soluble salt.

The second hydrophilic monomer is preferably selected from beta-acryloxypropionic acid, the water soluble salts of beta-acryloxypropionic acid (such as the alkali metal, ammonium, and lower alkyl quaternary amine salts of beta-acryloxypropionic acid), 2-hydroxyethyl methacrylate, ($C_1$–$C_4$)alkoxy($C_1$–$C_4$)alkyl and ($C_1$–$C_4$)alkoxy($C_1$–$C_4$)alkoxy($C_1$–$C_4$)alkyl acrylates and methacrylates, (meth)acrylate esters of $CH_3O(CH_2CH_2O)_xH$ where x is a positive integer from 2 to about 10, and the acrylate and methacrylate monoesters of $HO(CH_2CH_2O)_nH$ where n is a positive integer from 2 to about 10. Preferred second hydrophilic monomers include the water soluble salts of beta-acryloxypropionate, 2-hydroxyethyl methacrylate, 2-(2-methoxyethoxy)ethyl acrylate, 2-methoxyethyl acrylate, and the monomethacrylate ester of a polyethylene glycol having an average molecular weight of about 90. For example, sodium beta-acryloxypropionate, potassium beta-acryloxypropionate and diethylene glycol monomethacrylate can be used. When the second hydrophilic monomer is a carboxyl functional monomer, it is preferred that at least about 60% by weight of the second hydrophilic monomer be in the form of a water soluble salt, and it is especially preferable that substantially all the second hydrophilic monomer be in the water soluble salt form in this case. The second hydrophilic monomer is to be used in an effective amount.

The first and second hydrophilic monomers can be dissolved in an aqueous medium to form an aqueous monomer solution and subsequently copolymerized by conventional solution polymerization techniques. If desired non-ionized forms of the hydrophilic monomers, for example, acrylic acid and beta-acryloxypropionic acid, can be dissolved in an aqueous medium and subsequently neutralized to the extent desired by addition of a base, such as a concentrated aqueous solution of sodium hydroxide. Alternatively, water soluble salts of acrylic acid and beta-acryloxypropionic acid can be dissolved directly in the aqueous medium. In any case, the pH of the aqueous polymer solution is preferably adjusted, as by addition of a solution of alkali metal base, to shift the acid-base equilibrium so that substantially all the carboxylic acid functional monomers are in the form of anionic species.

As used in this specification and the claims, "(meth)acrylate" denotes both acrylate and methacrylate esters. Similarly, "(meth)acrylic acid" denotes both acrylic and methacrylic acid.

A batch polymerization technique can be employed. A single shot process in which all reactants are added to the polymerization medium before polymerization is initiated is preferred. However, other conventional polymerization techniques, such as continuous polymerization, single and multiple stage batch polymerization techniques, reverse suspension polymerization, and techniques employing gradual addition of reactants to the polymerization medium, can also be used.

Commercial grade acrylic acid can be used in the process of the present invention. The properties of commercial grade acrylic acid are described generally, for example, by L. S. Luskin in *Vinyl and Diene Monomers, Part 1*, (E. C. Leonard ed. Wiley-Interscience New York 1970) 105–203. Commercial grades of acrylic acid generally include small amounts of beta-acryloxypropionic acid, on the order of 1–1.5 percent by weight, id. at 169, which forms spontaneously. However, this level of beta-acryloxypropionic acid is not effective in the process of the present invention, and additional second hydrophilic monomer must be included in the monomer mixture employed in the present process.

Beta-acryloxypropionic acid is a head-to-tail dimer of acrylic acid which forms spontaneously in acrylic acid by the Michael addition reaction. Beta-acryloxypropionic acid, which is frequently present at low levels as an impurity in commercial grades of acrylic acid, can be recovered from acrylic acid distillate bottoms such as disclosed, for example, in U.S. Pat. Nos. 3,085,046 and 4,317,926. Crude fractions of of beta-acryloxypropionic acid, which tend to include higher head-to-tail oligomers of acrylic acid, can also be used. The second hydrophilic monomer, which can include beta-acryloxypropionic acid, one or more soluble salts of beta-acryloxypropionic acid, 2-hydroxyethyl methacrylate, one or more ($C_1$–$C_4$)alkoxy($C_1$–$C_4$)alkyl (meth)acrylate, one or more ($C_1$–$C_4$)alkoxy($C_1$–$C_4$)alkoxy($C_1$–$C_4$)alkyl (meth)acrylate, one or more mono(meth)acrylate ester of $HO(CH_2CH_2O)_nH$ where n is a positive integer from 1 to about 10, or a mixture of two or more of these species, comprises an amount effective to prevent phase separation otherwise observed shortly after polymerization is begun. This phase separation is observed in homopolymerization of soluble acrylate salts such as sodium acrylate, and is associated with reduced superabsorber performance properties. When the second hydrophilic monomer is a water soluble salt of beta-acryloxypropionic acid or mixture of water soluble salts of beta-acryloxypropionic acid, it is preferred that the second hydrophilic monomer comprise at least about 2% by weight of the total monomer. More preferably, in this case, the second hydrophilic monomer comprises at least 5% by weight of the total monomer.

Without being bound by any particular theory or explanation, it is currently thought that the significant improvement observed in the absorption capacity of the polymeric compositions of the present invention is associated with the fact that phase separation is not visually observed during the early stage of polymerization, or at other times during the polymerization, when the process of the present invention is used. This behavior contrasts with that observed, for example, during homopolymerization of sodium acrylate, where incipient phase separation is observed after polymerization has begun.

At least enough second hydrophilic monomer must be used to obtain the desired elimination of early phase separation which would otherwise be observed. The early phase separation is observed when highly neutralized acidic monomer is employed, such as acrylic acid substantially completely neutralized with sodium hydroxide. In contrast, at low to moderate degrees of neutralization, such as about 50%, the initial phase separation is not observed.

Use of second hydrophilic monomer in an amount higher than an amount effective to eliminate early phase separation does not appear to further improve the absorption capacity of the hydrogel. In the case of superabsorbent compositions prepared using water soluble salts of beta-acryloxypropionic acid, little significant difference in absorption capacities is observed as the weight proportion of second hydrophilic monomer is varied from about 5 to 20 percent by weight of total monomer. In general high levels of the second hydrophilic monomer are not favored because the absorption capacity per unit weight of superabsorbent polymeric composition is reduced. For example, when beta-acryloxypropionate (formula weight=143) is substituted for acrylate (formula weight=71), the number of carboxylate anions per unit weight being is reduced. A similar but more precipitous reduction in carboxylate anions per unit weight occurs when a nonionizable, second hydrophilic monomer, such as 2-methoxyethyl acrylate, is employed at high levels.

Both purified and crude preparations of beta-acryloxypropionic acid can be used. However, crude preparations, such as obtained from distillate bottoms resulting from the synthesis of acrylic acid from propylene or acrolein, contain substantial amounts of higher oligimers of acrylic acid, such as trimers and tetramers. For example, a crude preparation of beta-acryloxypropionic acid can contain about 50% by weight dimers (i.e., beta-acryloxypropionic acid) and about 50% by weight higher mers of acrylic acid. A purified preparation of beta-acryloxypropionic acid, made by distilling a crude preparation, can contain about 90% by weight beta-acryloxypropionic acid, 1-2% acrylic acid, and 8-9% trimer of acrylic acid (i.e., epsilon-acryloxy-n-pentanoic acid). Purified beta-acryloxypropionic acid is preferred, in that the absorption capacity of superabsorbent polymeric compositions prepared using the purified material will be greater than those prepared using the crude material since the number of carboxylate anions per unit weight of monomer will be greater for the purified material (lower average molecular weight)

In addition to the first and second hydrophilic monomers, the monomer which is polymerized to form the superabsorbent polymer composition of the present invention can include small amounts, for example, up to about 10 percent by weight, of other copolymerizable ethylenically unsaturated monomers, especially monomers which have at least some solubility in aqueous solutions. However, inclusion of other ethylenically unsaturated monomers in the monomer from which the polymeric composition is polymerized is generally not favored because the number of carboxylate groups per unit weight of the polymeric composition, and concomitantly, the absorption capacity, generally declines when such other monomers are substituted for water soluble acrylate salts. When such additional monomers are used, however, additional monoethylenically unsaturated monomers which are hydrophilic are preferred, especially those hydrophilic monoethylenically saturated monomers which are not effective as second hydrophilic monomers.

Examples of hydrophilic monoethylenically unsaturated monomers include: other carboxyl-functional monomers such as methacrylic acid, ethacrylic acid, crotonic acid, cinnamic acid, alpha-chloroacrylic acid, alpha-phenylacrylic acid, maleic acid, fumaric acid, itaconic acid, citraconic acid, succinic acid, mesaconic acid, glutaconic acid, aconitic acid, and the corresponding water soluble salts, such as sodium methacrylate, dipotassium maleate, sodium hydrogen fumarate, and the like; carboxyl anhydride-functional monomers such as maleic anhydride, other acid-functional monomers such as sulfonic acid-functional monomers, for example, 2-acryl-amido-2-methylpropane sulfonic acid, 2-hydroxy-3-acryloxy propane sulfonic acid, sulfopropyl methacrylate, and sulfoethyl acrylate, and the corresponding water soluble salts; other vinyl sulfonic acids such as vinyl sulfonic acid itself, styrene sulfonic acid, and vinyl toluene sulfonic acid; as well as phophonic acid-functional monomers such as phosphoethyl methacrylate; acrylate and methacrylate esters of water soluble polyethers; and water soluble acrylate and methacrylate esters of copolymers, including block copolymers, of propylene oxide and ethylene oxide; hydroxyalkylacrylates and methacrylates including 3-hydroxylpropyl acrylate and 2-hydroxyethyl acrylate; copolymerizable derivatives of natural products such as the allyl oligosaccharides disclosed in U.S. Pat. No. 4,587,319; and the like. Whether a specific hydrophilic monomer is effective as a second hydrophilic monomer can depend on the specific process conditions employed and can be determined by routine experimentation.

Other ethylenically unsaturated monomers which can be copolymerized with the first and second hydrophilic monomers include lower alkyl esters of ethylenically unsaturated carboxylic acids such as ethyl acrylate, methyl methacrylate, n-butyl acrylate, t-butyl acrylate, 2-ethylhexyl acrylate and methyl acrylate. These can be in amounts from 0 weight percent of the total monomer up to the maximum amount soluble in aqueous polymerization medium. Higher levels, which may require surfactant to be solubilized, are not favored.

In addition to the monoethylenically unsaturated monomers, the monomer which is polymerized to form the compositions of the present invention preferably includes at least one polyethylenically unsaturated copolymerizable monomer to crosslink and insolublize the product of the polymerization to form a hydrogel. The amount of polyethylenically unsaturated monomer required to form the gel depends upon a number of factors, such as the ratio of initiator to monomer, the functionality of the multi-functional monomer, the reactivity ratios of the monomers, as well as other factors, as is known in the polymerization art.

Preferably, the amount and type of the polyethylenically unsaturated monomer are selected to simulatenously maximize the water absorption capacity and the retention of the superabsorbent polymeric composition. The polyethylenically unsaturated monomer is preferably soluble in the aqueous monomer solution. However, if necessary, solubilizing agents such as nonionic surfactants can be added to the polymerization medium such as disclosed in U.S. Pat. No. 4,286,082. Examples of polyethylenically unsaturated monomers which can be used include diacrylates and dimethacrylates, such as diacrylates and dimethacrylates of alkendiols such as 1,4-butanediol, 1,5-pentanediol, and 1,6-hexanediol, poly(ethyleneglycol) dimethacrylates and diacrylates, ethyl-eneglycol diacrylate, ethyleneglycol dimethacrylate, propyl-eneglycol dimethacrylate, diethyleneglycol diacrylate, diethyleneglycol dimethacrylate, tetraethyleneglycol dimethacrylate, tetraethyleneglycol diacrylate, trimethylolpropane triacrylate, trimethylolpropane trimethacrylate, tetraerythritol diacrylate, tetraerythritol tetramethacrylate, pentaerythritol trimethacrylate, allyl methacrylate, and allyl acrylate; polyallyl compounds such as triallylisocyanurate, diallylphthalate, diallylamine, diallylacrylamide, diallylmethacrylate, diallylether, diallylmethylether, and polyallysaccharides such as diallylsaccharides; polyacrylamides such as N,N'-methylene bisacrylamide and N,N'-methylene bis methacrylamide and other polyvinyl crosslinking agents such as divinyl benzene and divinyl toluene. One presently preferred polyethylenically unsaturated comonomer is a poly(ethylene glycol) dimethacrylate having a number average molecular weight of about 600 for poly(ethylene glycol).

The polyethylenically unsaturated monomer is preferably added to the polymerization medium before polymerization is initiated. However, the polyethylenically unsaturated monomer can be added continuously during the polymerization reaction or it can be added to the polymerization medium after initiation. In one preferred embodiment, from about 0.02 to 0.75 percent by weight of monomer of poly(ethylene glycol) dimethacrylate ($M_n=600$ for polyethylene glycol) is preferred, and from about 0.05 to 0.20 percent is especially preferred.

In addition, or as an alternative, to crosslinking by copolymerization of at least one polyethylenically unsaturated monomer, crosslinking and insolublization can be accomplished by first polymerizing the monoethylenically unsaturated monomer and by subsequently reacting carboxyl functional groups pendent from the individual polymer chains formed in the polymerization reaction with a suitable chemical crosslinking agent, such as a compound having at least two functional groups reactive with the carboxyl group. Such crosslinking agents are well known in the art and examples include polyepoxides such as ethyleneglycol diglycidyl ether, propylethyleneglycol diglycidyl ether, and diethyleneglycol diglycidyl ether; haloepoxyalkenes such as epichlorohydrin, epibromohydrin, and 2-methyl epichlorohydrin; polyhaloalkanols such as 1,3-dibromoisopropanol and 1,3-dichloropropanol; and polyaziridines such as the triaziridine adduct of trimethylolpropane tripropionate (sold under the tradename TAZ by Aceto Chemical Company), tris(1-aziridinyl) phosphine oxide and 2,4,6-trisariridinyl-s-triazine.

A third alternative is to include a monoethylenically unsaturated copolymerizable monomer which bears a functional group which can react with carboxyl or carboxylate to form a covalent crosslink with a pendent carboxyl or carboxylate group on another polymer chain. Examples of such monomers include epoxy functional acrylates and methacrylates, such as glycidyl methacrylate, glycidyl acrylate, and N-methylol-functional monomers such as N-methylol acrylamide and N-methylol methacrylamide. Other di- and polyfunctional crosslinking agents include diols and polyols which link polymer chains through diesterification, di- and polyamines, and like.

Other types of crosslinking, such as ionic crosslinking of carboxylate groups in different chains by polyvalent metal compounds such as weak acid salts of zinc can also be used.

Other means of crosslinking the polymer chain can also be used, such as by exposing a solution containing the polymer or the dried polymer itself to ionizing radiation or high energy particles to generate highly reactive free radicals by bond scission.

Polymerization of the ethylenically unsaturated polymer can be effected by conventional techniques. The free radical polymerization of acrylic acid in aqueous solution is reviewed, for example, in R. A. M. Thomson, *Chemistry and Technology of Water Soluble Polymers* (C. A. Finch, ed. Plenum Press, N.Y. 1981) 53–70. Examples of polymerization initiators which can be employed include polymerization initiators of the free radical type, such as water soluble initiators including hydrogen peroxide, cumene peroxide, benzoyl peroxide, caprylyl peroxide, di-tert-butyl peroxide, tert-butyl diperphthalate, tert-butyl perbenzoates, soluble peracetate and percarbonate salts and ammonium or alkali metal (e.g., potassium, sodium or lithium) persulfate. The initiator can be used alone or as the oxidizing component of a redox system, which also includes a reducing component such as L-ascorbic acid or an alkali metal sulfite; more specifically a hydrosulfite, hyposulfite or metabisulfite, such as sodium hydrosulfite, potassium hyposulfite and potassium metabisulfite; or sodium formaldehyde sulfoxylate. The reducing component is frequently referred to as an accelerator. The initiator and accelerator, commonly referred to as catalyst, catalyst system or redox system, can be used in proportion from 0.0001% to 3% each, based on the weight of monomers to be copolymerized. Activators such as chloride and sulfate salts of cobalt, iron, nickel or copper can be used in small amounts. Examples of redox catalyst systems include tert-butyl hydroperoxide/sodium formaldehyde sulfoxylate/Fe(II), and ammonium persulfate/sodium bisulfite/sodium hydrosulfite/Fe(II). The polymerization temperature can be from room temperature to about 90° C., and can be optimized for the catalyst system employed, as is conventional. If desired, the initiator can be dissolved in an aqueous medium and gradually added to the monomer mixture such that the ratio of free radicals from the initiator to monomer is maintained at a low level during the polymerization.

The polymerization conditions in general should be selected to provide high molecular weight, lightly crosslinked, polymer compositions having a low soluble fraction. Each polymer chain should ideally be connected to the gel by a minimum number of crosslinks for optimum performance. As noted above, because there is a statistical distribution of crosslinks in practice, maximum swellability occurs when there is a significant percentage of uncrosslinked or soluble polymer chains. For approximately 100% neutralized acrylate-beta-acryloxypropionate copolymer prepared from a 40 weight percent aqueous solution and having an estimated molecular weight between about 600,000 and 1,000,000, the soluble fraction which optimizes swellability is from about 0.15 to 0.3 (15–30 weight percent).

If desired, small amounts of additives such as surfactants, water miscible organic cosolvents, and the like, can be employed in the polymerization medium. Small amounts of surfactants can be added to the aqueous monomer solution to improve monomer compatibility, especially when relatively hydrophobic multifuctional monomer is used, and helps to improve the wetting of the drying surface (belt drier or drum drier) and improve releasability of the partially dried material. Anionic surfactants such as alkyl sulfates, alkylaryl sulfonates, fatty acid soaps, monoglyceride sulfates, sulfoether esters, and sulfoether N-alkyl amides of fatty acids, can be used. Similarly nonionic surfactants can be employed, such as poly(alkeneoxy) alkanols of alkyl phenols and alkyl creosols, and poly(alkeneoxy) derivatives of aliphatic alcohols and other hydroxy compounds, carboxyl compounds, and carboxylic acid amides and sulfonamides. A preferred surfactant is Triton ® (trademark of Rohm and Haas Co.) X-100 (octylphenoxy(ethyleneoxy) ethanol). The proportion of surfactant employed depends upon the type of surfactant used and the ultimate use intended for the superabsorbent polymeric composition, and can vary from 0 to about 10% by weight of monomer. Preferably, the level of surfactants is from about 0.1 to about 5 percent by weight of monomer. When non-ionic surfactants such as Triton X-100 are used, it is preferable to use the non-ionic surfactant at a level of from about 0.2 to about 1 percent by weight of monomer.

The monomer concentration should be as high as the solubility of the monomer in the solvent allows to minimize the amount of solvent water which must be removed during drying. It is preferred that the monomer mixture be substantially completely neutralized, as by addition of an effective amount of an alkali metal base, before polymerization is begun. When the acid monomer is substantially completely neutralized, the pH of the polymeric compositions, product is found to be about 7 to 8. Prior art processes, employing acrylic acid to prepare superabsorbent polymeric composition typically only partially neutralize the monomer before the polymerization to give a superabsorbent polymeric product with a pH of from about 6 to 7.

Aqueous monomer compositions including initiator can be applied directly to the belt of a belt drier or drying surface of a single, double, or twin rotary drum drier and heated to polymerize and dry the polymerized hydrogel compositions to form superabsorbent material. For example, monomer composition can be polymerized and dried at temperatures between about 90° and 175° C. The proportion and type of initiator used, the monomer concentration, the thickness of the layer of monomer composition applied to the drying surface, whether a small amount of surfactant has been added to facilitate the release of partially dried material, and the like, can be optimized for specific heating and drying equipment by routine experimentation. The drying conditions can be adapted to provide to improved wet-out and reduced particle agglomeration such as disclosed in U.S. Pat. Nos. 4,127,944 and 4,043,944.

After the monomer has been polymerized and the resulting composition has dried to a solid having less than about 20% by weight water content, the solid can be granulated by using conventional pulverizing equipment such as a hammer mill. The resulting powder can be dried further to attain a moisture content of from about 2 to 7% by weight, assuming the initial drying did not reduce the moisture content to this range. The resulting superabsorbent polymeric composition can be used as is in manufacturing superabsorbent products such as disposable diapers, tampons, incontinence pads, sanitary napkins, panty liners, paper towels, facial tissues, and the like. Alternatively, specific particle size ranges of the superabsorbent powder can be selected by conventional means such as by sieving.

Alternatively, the hydrogel superabsorbent polymeric composition resulting from the polymerization can be used to coat fiberous materials, especially hydrophilic fibers, such as wood pulp (cellulose) fibers, rayon fibers, and polyester fibers. For example, the wet laying technique disclosed in U.S. Pat. No. 4,610,678 can be used for prepare absorbent structures of hydrogel-pulp fiber mixtures which are in turn useful in absorbent articles such as disposable diapers and the like.

For superabsorbent products such as disposable diapers and sanitary goods, the desired swelling time is on the order of ten minutes and the applied pressure encountered in the application is from about 0.5 to 1.5 psi. The capacity and retention properties of superabsorbent polymeric compositions can be measured by sealing a small amount of the superabsorbent polymeric composition in a tea bag and immersing the bag in a testing fluid. The superabsorbent composition, often in the form of a powder, swells within the tea bag. Swelling is limited only by the resistance imposed by the tea bag fabric, and the inherent swellability of the superabsorbent composition.

Since the superabsorbent compositions of the present invention are polyelectrolytes, their capacities depend on the ionic strength of the liquid to be absorbed. The capacity of polyelectrolyte superabsorbent materials declines with ionic strength. Thus, while tea bag capacities in the deionized water may range from 300 grams to 600 grams and even up to 1,000 grams of absorbed water per gram of superabsorbent composition, absorption of body fluids in substantially less because body fluids contain dissolved salt and have a concomitantly higher ionic strength than does water. Tea bag capacities for synthetic urine, which is believed to be representative of the results obtainable with actual body fluids such as blood and urine, range from about 30 to about 70 grams per gram for the superabsorbent polymeric compositions of this invention. Those superabsorbent compositions of the present invention which exhibit a minimum amount of fluid loss under applied pressure (about 1-5 gram per gram) at an applied pressure of 0.5 psi show capacities from about 40 to 50 gram per gram. The retention capacity of the tea bag is measured by determining the amount of fluid retained by the hydrogel after applying 0.5 psi (gauge) pressure for five minutes.

Unexpectedly, including the second hydrophilic monomer in the monomer from which the superabsorbent polymeric composition are polymerized increases the absorption capacity. Superabsorbent polymeric compositions prepared using monomer which includes from about 5 to 20% by weight of the second hydrophilic monomer shows capacity increases of up to as much as 20% by weight in comparison to polyacrylate controls.

In addition to their use in disposable diapers and the like, the superabsorbent polymeric compositions of this invention can also be used in coating seeds such as disclosed in U.S. Pat. No. 4,344,979, in manufacturing surgical drapes, as lost circulation additives for aqueous drilling muds such as disclosed in U.S. Pat. No. 4,664,816, and in a variety of other applications as will be apparent to those skilled in the art.

The following examples are illustrative of the process and composition of the present invention and will be useful to one of ordinary skill in the art in practicing the invention. However, the invention is in no way limited by these examples.

Example 1—Preparation of Superabsorbent Powder

A one gallon glass jar that had been thoroughly rinsed with deionized ("DI") water was charged with 700 g of acrylic acid and 77.8 g of distilled beta-acryoxypropionic acid ("AOPA") and 1060.5 g DI water and cooled to 5° C. with a salt/ice bath. This solution was neutralized with 725 g of 50% reagent grade NaOH added dropwise with stirring from a 1 liter addition funnel. The temperature of the solution was maintained below 35° C. As the addition neared completion a pH meter was connected to the solution and additional NaOH solution, about 35 g, added dropwise until the pH of the solution reached 8.0. This final addition had to be done slowly because the solubility limit of sodium acrylate was reached and some temporary precipitate often formed. The final solution had 36% solids.

A portion of the monomer solution was charged with crosslinker, initiator and surfactant just prior to polymerization according to the following formulation:

| monomer solution | 700.0 g |
| 10% w/w polyethyleneglycol (600 MW) dimethacrylate | 2.52 g |
| 10% w/w ammonium persulfate | 1.26 g |
| 10% w/w Formopon ® (trademark of Rohm and Haas Co., sodium formaldehyde sulfoxylate) | 0.45 g |
| 10% w/w Triton ® (trademark of Rohm and Haas Co.) X-100 | 12.6 g |

All solutions were in DI water. The reaction mixture was placed in a shallow tray with either a glass or Teflon ® (trademark of E.I. DuPont de Nemours Co.) lining in such an amount to give a liquid layer with a thickness of 75 mils. The tray was placed in an oven set at 175° C., covered with aluminum foil initially for a few minutes while polymerization was begun. Thereafter the foil was removed and the material was allowed to polymerize for 30 to 45 min. The resulting polymer had less that 20% w/w water content, and was ground to a powder in a Mikropulverizer ® (trademark of Bantam) hammermill. The powder was dried to a final water content of from 2 to 7% w/w, and the dried powder was sieved on a Rototop (trademark of Tyler) sifter to isolate a fraction having particle sizes between 50 and 40 mesh (300 to 420 microns).

Examples 2–21 and Comparative Examples

Using essentially the preparative method of Example 1, additional Examples 2–17 of superabsorbent powders including AOPA, Examples 18–21 of superabsorbent powders including other second hydrophilic monomers, and Comparative Examples 1–5, which omitted second hydrophilic monomers, were prepared as shown in Table I. The reaction mixtures were placed in the shallow trays in an amount sufficient to give a liquid layer with a thickness from 30 to 250 mils. The polymerization temperature varied from 90° to 175° C. Thinner film polymerizations were usually dry, i.e. <10% moisture, at the finish. The finished polymer was dried to less than 20% water content if the polymerization conditions did not already achieve that level. Drying conditions were 105° C. in a forced air oven for times up to over night depending on the thickness of the gel. Once at 20% or below, the polymer was hard enough to grind to powder in a hammermill. If necessary, the ground powder was given an additional drying treatment at 105° C. so that the final water content was in the range of 2 to 7%. The powder was sieved to isolate the particle size fraction between 50 and 40 mesh.

TABLE I

| Example or Comparative Example | Second Hydrophilic Monomer wt % | PEGDMA wt % | Polymerization Temperature C.° | Film Thickness (mil) |
|---|---|---|---|---|
| Comp. Ex. 1[1] | 0 | 0.3 | 175 | 75 |
| 1[1] | 10 AOPA | 0.3 | 175 | 75 |
| Comp. Ex. 2[1] | 0 | 0.3 | 175 | 75 |
| 2[1] | 9 AOPA | 0.3 | 175 | 75 |
| Comp. Ex. 3[2] | 0 | 0.15 | 175 | 75 |
| 3[2] | 5 AOPA | 0.15 | 175 | 75 |
| 4[2] | 10 AOPA | 0.15 | 175 | 75 |
| 5[2] | 20 AOPA | 0.15 | 175 | 75 |
| 6[2] | 20 AOPA | 0.15 | 175 | 75 |
| Comp. 4[2] | 0 | 0.15 | 175 | 75 |
| 7[2] | 2 AOPA | 0.15 | 175 | 75 |
| 8[2] | 5 AOPA | 0.15 | 175 | 75 |
| 9[2] | 10 AOPA | 0.15 | 175 | 75 |
| 10[2] | 20 AOPA | 0.15 | 175 | 75 |
| Comp. 5[3] | 0 | 0.10 | 90 | 250 |
| 11[3] | 5 AOPA | 0.10 | 90 | 250 |
| 12[3] | 5 AOPA | 0.10 | 90 | 250 |
| 13[3] | 10 AOPA | 0.10 | 90 | 250 |
| 14[3] | 10 AOPA | 0.10 | 90 | 250 |
| 15[3] | 14 AOPA | 0.10 | 90 | 250 |
| 16[3] | 20 AOPA | 0.10 | 90 | 250 |
| 17[3] | 20 AOPA | 0.10 | 90 | 250 |
| 18[2] | 5 MEA[4] | 0.3 | 175 | 75 |
| 19[2] | 5 MEEA[5] | 0.3 | 175 | 75 |
| 20[3] | 4 MEA[4] | 0.3 | 175 | 75 |
| 21[3] | 5 PE-90[6] | 0.3 | 175 | 75 |

[1]0.5% ammonium persulfate, 0.18% Formopon ®, 0.5% Triton ® X-100
[2]0.05% ammonium persulfate, 0.018 Formopon ®, 0.5% Triton ® X-100
[3]0.05% ammonium persulfate, 0.018% Formopon ®
[4]MEA = 2-methoxyethyl acrylate
[5]MEEA = 2-(2-methoxyethoxy)ethyl acrylate
[6]PE-90 = polyethylene glycol (molecular weight of about 90) monomethacrylate (GCA Chemical)

A sample of each powder weighing 0.2 g was heat sealed in a two inch square tea bag prepared from paper supplied by the Dexter Co. The tea bag was immersed in synthetic urine containing 1.2% salt by weight. The synthetic urine had the weight composition:

| deionized water | 900 |
| calcium phosphate, monobasic | 0.309 |
| potassium phosphate | 0.681 |
| magnesium sulfate.7H$_2$O | 0.477 |
| potassium sulfate | 1.333 |
| sodium phosphate.12H$_2$O | 1.244 |
| sodium chloride | 4.441 |
| potassium chloride | 3.161 |
| sodium azide | 0.4 |
| urea | 8.56 |
| Pluronic ® (trademark of BASF Wyondotte Corp. for block copolymer surfactants) 10R-8 | 0.1 |
| deionized water | To 1000 total |

After a 10 minute soak the excess water was removed by laying the bag on a paper towel for one minute. The weight of the bag was determined and the capacity calculated after a correction for the weight of the wet tea bag fabric. Retention capacity was determined by allowing the same bag to reswell for one additional minute followed by the application of 0.5 psi pressure for 5 minutes using a vacuum box. The capacity was calculated as above to give the retention while the ratio of retention to 10 minute capacity gives a measure of the resistance to loss of fluid under pressure.

Soluble fractions were determined by placing 0.5 g of powder in 200 g of saline solution. The solution was stirred for 30 minutes, allowed to stand overnight and finally stirred for another 30 min. The mixture was filtered through a Buchner funnel with coarse filter paper and 37.5 g of ethanol added to 112.5 g of filtrate. The resulting mixture was titrated with 0.5N HCl and then back titrated with 0.5N NaOH.

For the comparative examples, the weight of sodium acrylate in mg equals the milliliters HCl times 47, while the weight of acrylic acid equals the milliliters of NaOH minus those of HCl times 36. The soluble fraction is the sum of the two weights divided by 112.5/200 times the original sample weight.

Table II illustrates the performance of superabsorbent compositions of materials the invention with comparative materials obtained by acrylic acid polymerization. A number of different polymerization conditions are repeated. Materials of similar soluble fractions are compared. It can be seen that advantages in both 10 minute capacity and retention capacity appear when about 5% by weight second hydrophilic monomer is included in the monomer mix. Often a higher percentage of capacity is retained after application of pressure when second hydrophilic monomer is present.

TABLE II

| Example or Comparative Example | Second Hydrophilic Monomer (wt %) | Tea Bag Capacity 10 min. (g/g) | Tea Bag Capacity Retention (g/g) | Tea Bag Capacity ret./10 min. (%) | Soluble Fraction (%) |
|---|---|---|---|---|---|
| Comp. Ex. 1 | 0 | 34.2 | 32.8 | 96 | 30 |
| 1 | 10 | 43.7 | 41.8 | 96 | 38 |
| Comp. Ex. 2 | 0 | 32.9 | 31.9 | 97 | 34 |
| 2 | 9 | 46.4 | 45.9 | 99 | 31 |
| Comp. Ex. 3 | 0 | 41.9 | 36.0 | 86 | 29 |
| 3 | 5 | 41.8 | 40.7 | 97 | 33 |
| 4 | 10 | 53.3 | 52.9 | 99 | 24 |
| 5 | 20 | 48.9 | 48.0 | 98 | 30 |
| 6 | 20 | 49.5 | 50.2 | 101 | 30 |
| Comp. Ex. 4 | 0 | 27.8 | 29.1 | 105 | 45 |
| 7 | 2 | 28.5 | 28.9 | 101 | 45 |
| 8 | 5 | 32.2 | 32.7 | 102 | 41 |
| 9 | 10 | 40.0 | 41.7 | 104 | 38 |
| 10 | 20 | 38.1 | 37.7 | 99 | 40 |
| Comp. Ex. 5 | 0 | 50.0 | 44.1 | 88 | 20 |
| 11 | 5 | 54.5 | 52.4 | 96 | 24 |
| 12 | 5 | 55.7 | 50.7 | 91 | 24 |
| 13 | 10 | 57.5 | 51.5 | 90 | 18 |
| 14 | 10 | 56.4 | 55.6 | 99 | 24 |
| 15 | 14 | 56.8 | 55.4 | 98 | 18 |
| 16 | 20 | 59.36 | 53.1 | 90 | 22 |
| 17 | 20 | 58.2 | 56.3 | 97 | 25 |
| 18 | 5 | 53.0 | 48.4 | 91 | 15 |
| 19 | 5 | 43.4 | 42.1 | 97 | 30 |
| 20 | 4 | 51.0 | 49.0 | 96 | 25 |
| 21 | 5 | 50.0 | 42.0 | 84 | 12 |

Comparative Examples 6 and 7

A 1 liter resin kettle was charged with 500 g of aqueous sodium acrylate solution (36% solids, pH=8). Next 0.16% sorbitan monolaurate (0.29 g) and 0.15% poly(ethylene glycol) dimethacrylate (molecular weight of polyethylene glycol=600) (0.27 g) were added to the monomer solution. The mixture was then sparged with bubbling nitrogen for 30 minutes. After the sparge the mixture was placed under positive nitrogen pressure and and warmed to 40° C. Ammonium persulfate (0.038%, 0.07 g dissolved in 5 ml water) and sodium formaldehyde sulfoxylate (0.013%, 0.02 g dissolved in 5 ml water) were then added. The temperature and appearance of the reaction mixture were visually monitored. Phase separation was observed at an early point in the reaction. After the reaction mixture had reached its maximum temperature it was allowed to cool slowly to room temperature, before it was removed from the kettle. The hydrogel was cut into small pieces and dried overnight at 105° C. It was then ground and sieved to give a superabsorbent powder. The absorption and retention capacity and the soluble fraction were measured and the results are reported in Table III.

Examples 22–27 and Comparative Examples 8 & 9

The preparative process and evaluation of Comparative Examples 6 and 7 were repeated to prepare Examples 22–26 and Comparative Examples 8 and 9, except that the monomer solution contained a second hydrophilic monomer in the amount indicated in Table III.

These examples and comparative examples demonstrate that second hydrophilic monomers which eliminate the phase separation improve the product performance, whereas those that do not eliminate the phase separation have little effect on product performance.

TABLE III

| Example or Comparative Example | Monomer Composition Second Hydrophilic Monomer Wt % | PEGDMA Wt % | Tea Bag Capacity 10 Min g/g | Tea Bag Capacity Ret g/g | Tea Bag Capacity Ret/ 10 Min % | Soluble Fraction | Phase Separation[1] |
|---|---|---|---|---|---|---|---|
| Comp. Ex. 6 | none | 0.15 | 40.3 | 34.5 | 86 | 0.14 | yes |
| Comp. Ex. 7 | none | 0.05 | 42.3 | 37.8 | 89 | 0.25 | yes |
| Comp. Ex. 8 | NaMA[4] | 0.15 | 46.2 | 39.1 | 85 | 0.17 | yes |
| Comp. Ex. 9 | HEA[5] | 0.15 | 42.7 | 35.4 | 83 | 0.14 | yes |
| Ex. 22 | NaAOPA[2] | 0.15 | 52.7 | 49.6 | 94 | 0.34 | no |
| Ex. 23 | NAOPA | 0.25 | 48.3 | 48.9 | 101 | 0.30 | no |
| Ex. 24 | MEA[3] | 0.15 | 52.0 | 49.4 | 95 | 0.27 | no |
| Ex. 25 | HEMA[6] | 0.15 | 49.5 | 44.5 | 90 | 0.16 | no |
| Ex. 26 | PE-90[7] | 0.05 | 53.4 | 47.0 | 88 | 0.14 | no |

[1] visually observed during early stage of polymerization
[2] sodium salt of AOPA
[3] 2-methoxyethyl acrylate
[4] sodium methacrylate
[5] hydroxyethyl acrylate
[6] hydroxyethyl methacrylate
[7] polyethylene glycol (molecular weight of about 90) monoethacrylate (GCA Chemical)

We claim:

1. A process for the preparation of a superabsorbent polymeric composition for absorbing and retaining aqueous fluids, the process comprising:
   (a) preparing a monomer mixture including at least one first hydrophilic monomer selected from the group consisting of acrylic acid and the water soluble salts of acrylic acid, and an effective amount of at least one second hydrophilic monomer to at least reduce the extent of the phase separation of said mixture which would occur shortly after polymerization began in the absence of said second hydrophilic monomer;
   (b) adjusting the pH of said mixture prior to polymerization to substantially completely exclude the free acid forms of said first hydrophilic monomer and said second hydrophilic monomer: and
   (c) polymerizing said monomer mixture: wherein said second hydrophilic monomer is selected from beta-acryloxypropionic acid, the water-soluble salts of beta-acryloxypropionic acid, 2-hydroxyethyl methacrylate, the ($C_1$-$C_4$) alkoxy ($C_1$-$C_4$) alkyl (meth) acrylates, the ($C_1$-$C_4$) alkoxy ($C_1$-$C_4$) alkoxy ($C_1$-$C_4$)alkyl (meth) acrylates, the mono (meth) acrylate esters of $HO(CH_2CH_2O)_nH$ where n is a positive integer from 2 to about 10, and the (meth) acrylate esters of $CH_3O(CH_2CH_2O)_xH$ where x is a positive integer from 2 to about 10.

2. A process according to claim 1 wherein the monomer mixture includes a least one water-soluble salt of acrylic acid and a water-soluble salt of beta-acryloxypropionic acid, the salt of beta-acryloxypropionic acid being at least about five per cent by weight of the monomer mixture, the monomer mixture being polymerized in aqueous solution and the pH of the aqueous solution being adjusted to substantially exclude the free acid forms of acrylic acid and beta-acryloxypropionic acid.

3. A process according to claim 1 wherein the monomer mixture includes at least one water-soluble salt of acrylic acid, at least about five percent by weight of a water-soluble salt of beta-acryloxypropionic acid, and a crosslinking monomer including at least two polymerizable ethylenically unsaturated groups.

4. A process according to claim 3 wherein the at least one salt of acrylic acid is sodium acrylate and the salt of beta-acryloxypropionic acid is sodium beta-acryloxypropionate.

5. A process according to claim 3 wherein the crosslinking monomer is a polyethylene glycol dimethacrylate.

6. A process according to claim 1 wherein the second hydrophilic monomer is selected from 2-hydroxyethyl methacrylate, 2-methoxyethyl acrylate and 2-(2-methoxyethoxy)ethyl acrylate.

7. A process according to claim 1 wherein the second hydrophilic monomer is the mono methacrylate ester of a polyethylene glycol having an average molecular weight of about 90.

8. A process according to claim 1 wherein the second hydrophilic monomer is present in an amount effective to prevent the phase separation.

9. A process according to claim 1 wherein the monomer mixture is coated onto a heated surface, the heated surface elevating the temperature of the monomer mixture, thereby polymerizing the monomer and drying the, polymerized material.

10. A process according to claim 9 wherein the heated surface is provided by a heated belt of a belt drier.

11. A process according to claim 9 wherein the heated surface is provided by a heated drum of rotary drum drier.

12. A process according to claim 1 further comprising drying the superabsorbent material to a water content of less than about twenty percent by weight and pulverizing the dried material.

13. A process according to claim 12 further drying the powdered superabsorbent material to a water content in the range from about two to seven percent by weight.

* * * * *